US005756314A

United States Patent [19]

Ito et al.

[11] Patent Number: 5,756,314
[45] Date of Patent: May 26, 1998

[54] METHOD FOR PREPARATION OF MONOSIALOGANGLIOSIDE GM1

[75] Inventors: Makoto Ito, Fukuoka; Yasufumi Fukano, Fukuoka-ken, both of Japan

[73] Assignee: Takara Shuzo Co., Ltd., Kyoto-fu, Japan

[21] Appl. No.: 719,211

[22] Filed: Sep. 25, 1996

[30] Foreign Application Priority Data

Mar. 1, 1996  [JP]  Japan .................. 8-071246

[51] Int. Cl.⁶ .................. C12P 19/44; C12P 19/26; C12P 19/00
[52] U.S. Cl. .................. 435/84; 435/74; 435/253.3; 435/874
[58] Field of Search .................. 435/84, 74, 874, 435/253.3

[56] References Cited

U.S. PATENT DOCUMENTS 4,868,292  9/1989  Yokoyama et al. .
5,275,939  1/1994  Sugimori et al. .
5,296,360  3/1994  Sugimori et al. .

FOREIGN PATENT DOCUMENTS 0 319 890  6/1989  European Pat. Off. .
0 540 790  5/1993  European Pat. Off. .

OTHER PUBLICATIONS

Julian N. Kanfer, Methods in Enzymology, Preparation of Gangliosides, vol. 14, pp. 660–664 (1969).
Robert W. Ledeen et al., Methods in Enzymology, Gangliosides: Structure, Isolation . . . , 83, pp. 139–191.
APS Abstract JP63–291582 Morikawa et al (Nov. 29, 1985).

*Primary Examiner*—Herbert J. Lilling
*Attorney, Agent, or Firm*—Birch, Stewart, Kolasch & Birch, LLP

[57] ABSTRACT

A method for producing monosialoganglioside GM1 comprising the step of contacting a crude ganglioside mixture with a microorganism capable of producing a sialidase; and a bacterial strain of Pseudomonas genus capable of producing a sialidase and usable in the above method.

8 Claims, 5 Drawing Sheets

METHOD FOR PREPARATION OF MONOSIALOGANGLIOSIDE GM1

BACKGROUND OF THE INVENTION

1. Field of the Invention

Gangliosides are glycosphigolipids having one or more sialic acid residues, and found abundantly in the cerebral and nervous tissues of fish, mammals, etc. A number of studies have so far been conducted to elucidate the physiological functions of GM1, one monosialoganglioside species, and it is reported that monosialoganglioside GM1 (hereinafter sometimes simply referred to as GM1) modulates various biological functions including those of enzymes, ion-channels, and the receptors of platelet-derived growth factor (PDGF). Also, GM1 binds to CD4 of helper T-cells and exerts an anti-HIV action, suggesting the possibility that GM1 may be used for therapeutic agents for HIV. Recently, GM1 has been attracting attention as therapeutic agents for various neurological diseases including Alzheimer's disease and Parkinson's disease. In fact, clinical use of ganglioside preparations containing GM1 has already been introduced mainly into Europe and South America as a therapeutic agent for peripheral nervous diseases.

2. Discussion of the Related Art

Gangliosides are conventionally prepared from bovine brains by the method of Kanfer, J. N. (Methods in Enzymology, 14, 660–664 (1969)). Gangliosides are classified, depending on the number of linked sialic acid residues per molecule, into GM1, GD1, GT1, GQ1, etc. where "M" of GM1 indicates "monosialo" having one sialic acid residue; "D" of GD1 indicates "disialo" having two sialic acid residues; "T" of GT1 indicates "trisialo" having three sialic acid residues; and "Q" of GQ1 indicates "quaternary sialo" having four sialic acid residues.

The following methods are known for preparation of GM1:

(1) A crude ganglioside mixture obtained from bovine brains is heated up to 50° C. in a solvent containing alcohol or chloroform under acidic conditions to produce GM1 (U.S. Pat. No. 4,868,292); and (2) Bovine brains are disrupted and subjected to an autolysis treatment in the presence of a surfactant to produce GM1 (EP 0319890A1). These methods are not satisfactory in terms of yield and purity of GM1.

Also, the following methods utilizing a sialidase, an enzyme which acts on glycolipids to release sialic acid, are also known:

(3) A crude ganglioside mixture is heated together with a sialidase fixed on agarose gel, the sialidase (Sigma Type VIA) being produced by *Clostridium perfringens* (EP 0540790A1) to produce GM1;

(4) Sialidase isozyme S produced by *Arthrobacter ureafaciens* is used to produce GD1b and/or GM1 from a crude ganglioside mixture (U.S. Pat. No. 5,296,360); and (5) Sialidase isozyme L produced by *Arthrobacter ureafaciens* is used to produce GM1 and/or asialo GM1 (U.S. Pat. No. 5,275,939).

The above methods utilizing a sialidase are not advantageous in terms of production cost, because they use purified enzymes. Also, in the methods (4) and (5) above, the amount of GM1 produced in the reaction mixture depends on enzyme quantity, reaction time and other reaction conditions, and, therefore, these methods are by no means satisfactory in terms of efficiency and cost.

SUMMARY OF THE INVENTION

Accordingly, an object of the present invention is to provide a method which permits to produce a large quantity of GM1 efficiently and economically. Another object of the present invention is to provide a bacterium of Pseudomonas strain which is capable of producing a sialidase and which is usable in the method of the present invention.

In the present specification, the ganglioside having 2 or more sialic acid residues are referred to as polysialoganglioside. GM1 accounts for only 20% of the total gangliosides contained in the bovine brain. When GM1 is purified from the mixture without any pre-treatments, sufficient amount of GM1 cannot be obtained. The present inventors directed their attention to the solution to the above problem, and tried to seek a method for producing GM1 in large quantities, and found that a large quantity of GM1 can be obtained from a mixture of polysialogangliosides by culturing bacteria capable of producing a sialidase together with the mixture of polysialogangliosides and converting polysialogangliosides into GM1.

There are several bacterial strains known to produce a sialidase, but many of them, e.g. *Vibrio cholerae, Streptococcus pneumoniae*, and Newcastle disease virus, are pathogenic and their use is not desirable for production of GM1. Hence, the present inventors conducted a search for usable sialidase-producing bacteria in the ocean where unutilized and useful bacteria with relatively low pathogenesis to humans are thought to exist. As a result, the present inventors found that a certain type of bacterial strain produces a sialidase suitable for producing GM1 in large quantities and have completed the present invention.

In one embodiment, the present invention relates to a method for preparation of GM1, wherein a crude ganglioside mixture is made to contact with a microorganism capable of producing a sialidase.

In another embodiment, the present invention relates to a Pseudomonas strain capable of producing a sialidase.

The use of the production method of the present invention allows GM1 to be efficiently produced in large quantities at low cost.

DETAILED DESCRIPTION OF THE INVENTION

Figure 1:
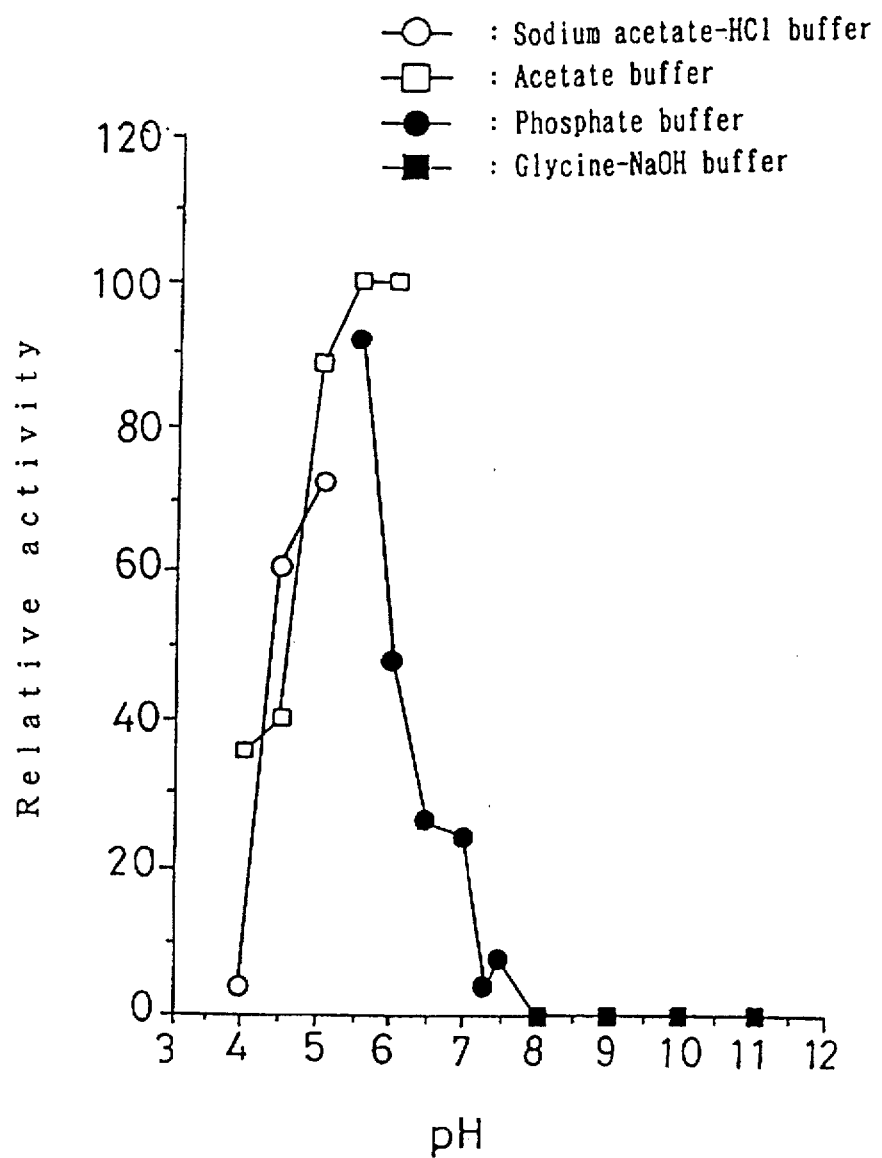
FIG. 1 shows optimal pH of the sialidase produced by the Pseudomonas strain of the present invention.

The present invention is described in more detail below.

In the present method where a crude ganglioside mixture is made to contact with a microorganism capable of producing a sialidase to yield GM1, the microorganism usable in the present invention is not particularly limited as long as it is a bacterial strain capable of producing sialidase, and variants thereof may also be used. Preferably, the sialidase produced gives no effect on GM1. The microorganisms may be isolated by adding a sample, such as seaweed, sea water, and beach sand, to a synthetic medium where ganglioside is the only carbon source, and cultivating the sample at 25° C. for 3 to 4 days. After the decomposition of the gangliosides in the culture supernatant is confirmed by TLC, the culture including sialidase activity is inoculated to a fresh medium. This procedure is repeated 3 to 4 times, and the colonies of the target microorganism can be obtained on a plate medium.

Specific examples of bacterial strains capable of producing a sialidase which does not affect GM1 include Pseudomonas strains such as Pseudomonas sp. YF-2. Pseudomonal sp. YF-2 is a halophilic strain which the present inventors first isolated from a sea water sample of Hakata Bay, which has the following bacteriological properties:

The observation with a transmission electron microscope revealed that the strain is a gram negative rod which has a 0.9 to 1.2 μm long and about 0.5 μm wide body with a very long monopolar flagellum. Table 1 shows the results of identification test of the present strain.

TABLE 1

| Form | Rods |
| --- | --- |
| Motility | + |
| Gram staining | − |
| Growth in aerobic conditions | + |
| Growth in anaerobic conditions | − |
| Catalase | + |
| Oxidase | − |
| O - F test | − |
| DNA decomposing ability | − |
| Gelatine liquefaction | − |
| Arginine dehydrogenase | + |
| Growth of bacteria at 5° C. and 37° C. | − |
| Growth on: | |
| Glucose | + |
| Trehalose | − |
| L-Arginine | − |
| L-Valine | − |
| β-Alanine | − |
| Production of fluorescent pigment | − |
| Content of G-C | 68.5% |

Based upon the above bacteriological properties, the identification of the strain was conducted according to the classification method of Bergey's Manual of Determinative Bacteriology, 8th ed., Williams & Wilkins Company, 1974. As a result, though it was confirmed that the bacteria obtained belong to Pseudomonas genus, no known species fit well in the above bacteriological properties. Thus, the bacterial strain obtained was identified as a novel oceanic Pseudomonas strain. The strain was designated as Pseudomonas sp. YF-2, and deposited under accession number FERM BP-6075 at the National Institute of Bioscience and Human-Technology, Agency of Industrial Science and Technology, Ministry of International Trade and Industry.

The enzymological and physicochemical properties of the sialidase produced in the culture medium by the strain of the present invention (hereinafter simply referred to as the present enzyme) are as follows.

(1) Action

The sialidase acts on a sialyl bond to release sialic acid.

(2) Substrate Specificity

The sialidase obtained acts on GM3, GD1a and sialyl lactose (SA-Lac) to release sialic acid, but not on GM1 and GM2 at all. That is, the present enzyme well acts on the non-reducing terminus sialyl bond of the sugar chain of gangliosides, whereas it does not act on the internal sialyl bond of the sugar chain (Table 2). This indicates that the sialidase produced by the novel bacterial strain has an action to convert polysialoganglioside to GM1.

TABLE 2

| Substrate Specificity | |
| --- | --- |
| | Decomposability (%) |
| GM1 | 0 |
| GM2 | 0 |
| GM3 | 55.3 |
| GD1a | 43.3 |
| GD1b | 27.0 |
| GD3 | 1.0 |
| GT1b | 27.7 |
| Sialyl-Lactose | 65.6 |

(3) Optimal pH and Heat Stability

Figure 2:
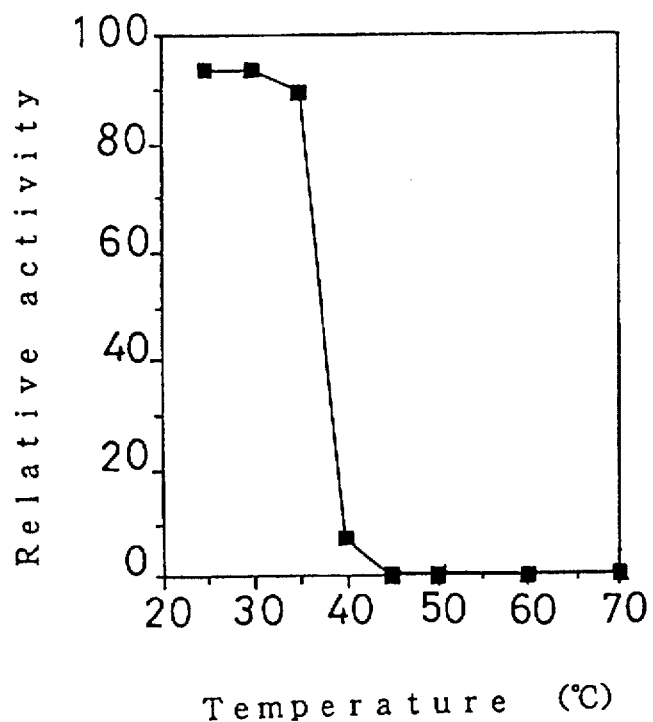
FIG. 2 shows heat stability of the sialidase produced by the Pseudomonas strain of the present invention.

The optimal pH of the present enzyme is 5.5, and it shows relatively high activity in the range of pH 4.5 to pH 6.0 (FIG. 1). When the present enzyme was kept in a 20 mM acetic acid buffer solution at pH 5.0 for 2 hours at varying temperatures, the present enzyme was found to be almost inactivated at temperatures of 40° C. or higher, and stable at relatively low temperatures of 37° C. or lower (FIG. 2).

(4) Influence of Metal Salts

The influence of various metal salts on the present enzyme was examined. Copper sulfate, zinc acetate, and chlorides of other metals are used. Each metal salt was added to the reaction system to make a 2 mM concentration. As shown in Table 3, it was found that the present enzyme is significantly activated by manganese or barium, and significantly suppressed by mercury, copper, or iron.

TABLE 3

| Influence of Metal Salts | |
| --- | --- |
| | Relative activity |
| None | 100 |
| $Hg^{2+}$ | 2 |
| $Cu^{2+}$ | 8 |
| $Ca^{2+}$ | 112 |
| $Mn^{2+}$ | 123 |
| $Mg^{2+}$ | 106 |
| $Fe^{2+}$ | 0 |
| $Zn^{2+}$ | 84 |
| $Ba^{2+}$ | 122 |

In the method for preparation of GM1 of the present invention, the bacterial strain and a crude ganglioside mixture may be made to contact each other for example in the manner that a crude ganglioside mixture is added to a nutrient broth where the strain as mentioned above has already been grown, or in the manner that the strain is cultured in a broth where a crude ganglioside mixture has already been added. In any cases, the amount of the crude ganglioside mixture added to the broth is not limited and determined case by case. In a preferred example, 1–2000 mg of crude ganglioside mixture is added to 100 ml of nutrient broth where the strain as mentioned above has already been grown, or the strain is cultured in 100 ml of broth where 1–2000 mg crude ganglioside mixture has already been added.

Here, the term "crude ganglioside mixture" means a ganglioside mixture prepared from, for example, bovine brains which contains various gangliosides species. The crude ganglioside mixture can be prepared by, for example, the method of Kanfer, J. N. (Methods in Enzymology, 14, 660–664 (1969)).

The culture media usable in the present invention are not particularly limited as long as they permit the growth of the bacterial strain, production of a sialidase by the strain, and efficient production of GM1 from a crude ganglioside mixture. As the carbon source for the media, crude ganglioside mixture and polysialogangliosides (GD1a, GD1b, GT1a, and GT1b) may be used, with a preference given to GD1a. As the nitrogen source, ammonium chloride and polypeptone may be suitably used.

Inorganic materials and metal salts, such as phosphates, potassium salts, magnesium salts and zinc salts, may be added to the media.

The production amounts of sialidase and GM1 depend on the culture conditions. GM1 is produced in 1–7 day shaking culture preferably at a temperature of from 20° to 35° C., and at a pH of from 7.2 to 7.4.

After the completion of the culture, the bacterial cells are removed from the culture broth containing the target GM1 for example by centrifugation, and proteins and salts are removed by conventional methods from the supernatant thus obtained. For example, it is effective to apply the supernatant to a reversed-phase $C_{18}$ column to remove proteins together with salts. From the desalted supernatant, GM1 can be purified by the method described in Methods in Enzymology, 83, 139–191 (1982). The structural identification of the purified GM1 is carried out by thin-layer chromatography, liquid chromatography, mass spectrometry, and nuclear magnetic resonance spectrometry.

By the method as mentioned above, gangliosides in a crude ganglioside mixture can be converted to GM1 preferably by cultivating the crude ganglioside mixture with the microorganism of the present invention.

EXAMPLES

The present invention is hereinafter described in more details by means of the following examples, but not limited by them in any ways.

Example 1

Isolation of Pseudomonas Strain Capable of Producing Sialidase

A sample of sea water was obtained from Hakata Bay in an amount of 0.01 mL and added to 0.1 mL of a synthetic medium (crude ganglioside mixture: 0.1% by weight, NaCl: 1% by weight, $NH_4Cl$:0.05% by weight, $K_2HPO_4$: 0.05% by weight, pH 7.4). The mixture was cultured at 25° C. for 3 days. The crude ganglioside mixture used here was obtained from bovine brain by the method of Kanfer, J. N. (Methods in Enzymology, 14, 660–664 (1969)). Thereafter, decomposition of the gangliosides in the supernatant of the medium was confirmed by TLC, and the strains showing a sialidase activity were cultured using a fresh preparation of the above-mentioned synthetic medium. This process was repeated three times in total, and colonies were obtained on a plate medium. As a result, 28 strains which are capable of producing sialidase were isolated. The strains were subjected to bacteriological analyses and identified according to the classification described in Bergy's Manual of Determinative Bacteriology, 8th ed., Williams and Wilkins Company, 1974. As a result, one of the strains was identified as a novel oceanic Pseudomonas strain and designated as Pseudomonas sp. YF-2. This strain was deposited under accession number FERM BP-6075 at the National Institute of Bioscience and Human-Technology, Agency of Industrial Science and Technology, Ministry of International Trade and Industry.

Example 2

(1) Culture of Microorganism and Conversion of Crude Ganglioside Mixture to Monosialoganglioside GM1

Figure 3:
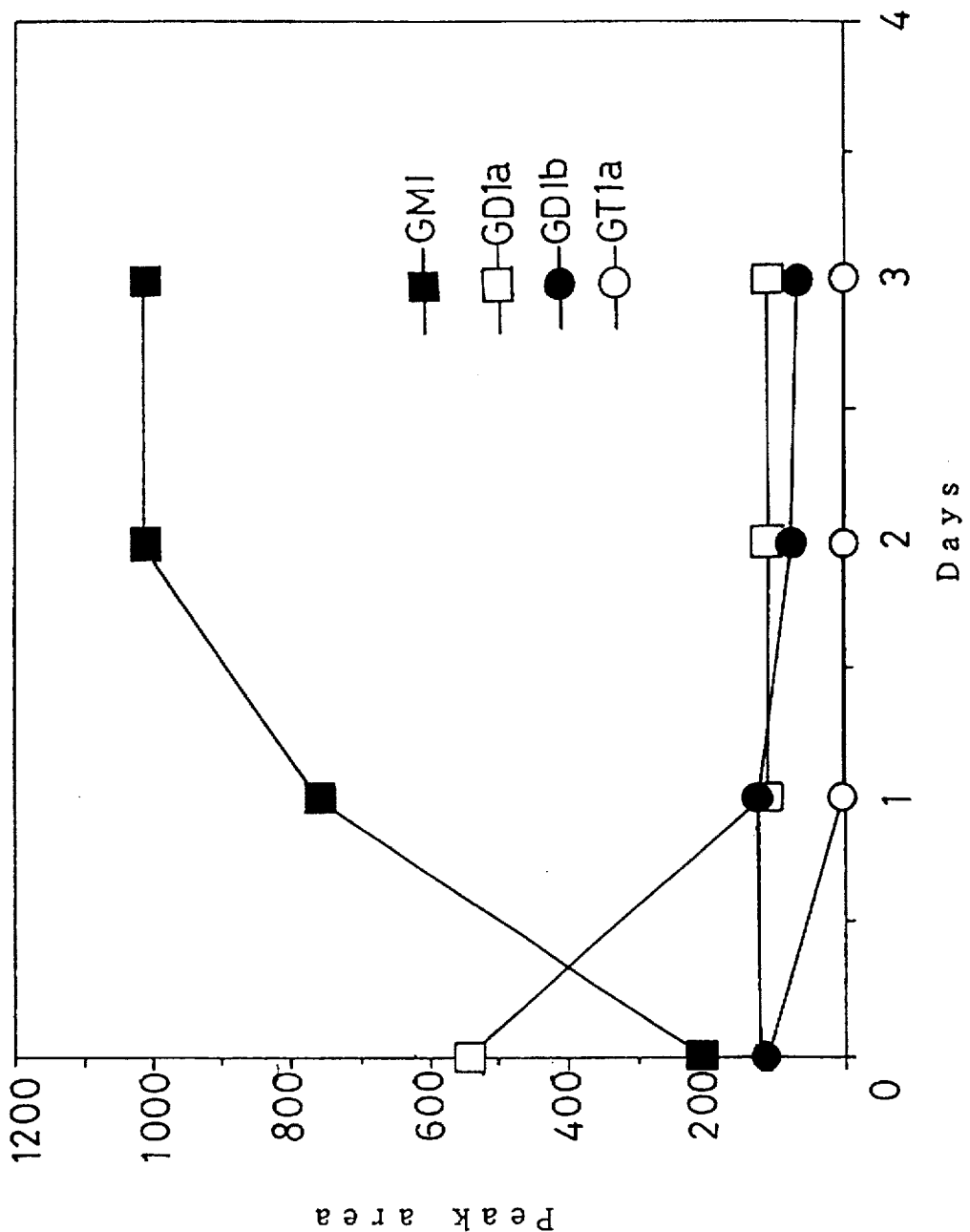
FIG. 3 shows the conversion of the crude ganglioside mixture into GM1 in Example 2.

A crude ganglioside preparation, a mixture of glycolipides, was prepared according to the method of Kanfer, J. N. (Methods in Enzymology, 14, 660–664 (1969)). In a 100-mL liquid medium ($K_2HPO_4$: 0.05% by weight, $NH_4Cl$:0.05% by weight, NaCl: 1% by weight, pH 7.4) containing 500 mg of the obtained crude ganglioside mixture, Pseudomonas sp. YF-2 was shaken-cultured at 25° C. for 3 days. After centrifugation, the supernatant was analyzed for monosialoganglioside GM1 content, revealing that the content of GM1 was increased from about 20% in the crude ganglioside mixture up to 90% or higher in the supernatant obtained after 3-day culture (FIG. 3). Incidentally, the quantification of each component was carried out as follows:

After the sample was subjected to TLC [chloroform/methanol/0.2% KCl=5:4:1(v/v)], orcinol sulfuric acid solution was sprayed over the plate. Then the plate was heated in an oven at 100° to 110° C. for 10 minutes. Using GM1 (Yatoron), GD1a (Yatoron), GD1b (Yatoron), and GT1a (Biocurve) as the standard samples, each component was quantified by determining the absorbance at 540 nm using a TLC chromatoscanner CS9300 (Shimadzu).

(2) Purification of GM1

The culture supernatant obtained by centrifuging the culture medium (containing about 200 mg gangliosides) was loaded on a reversed-phase $C_{18}$ column (preparative $C_{18}$, 125Å, manufactured by Millipore, packed amount of 30 g, column diameter of 30 mm, open column) which was previously washed with methanol and equilibrated with deionized water. After desalting by passing 300 ml of deionized water through the column, glycolipid was eluted by passing 500 mL of chloroform/methanol(2/1:v/v) through the column. The eluted fraction was concentrated with an evaporator, and subjected to anion exchange chromatography as mentioned below.

GM1 was purified by anion exchange column chromatography using DEAE Sephadex A25 (Pharmacia) according to the following procedures:

Chloroform/methanol/deionized water (30:60:8 (v/v)) was used as Eluent I; chloroform/methanol/0.8M sodium acetate aqueous solution (30:60:8 (v/v)) as Eluent II. DEAE Sephadex A25 (75 mL) equilibrated in Eluent I was packed in a column with a diameter of 25 mm (open column). About 200 mg of gangliosides was dissolved in 50 mL of Eluent I, and subjected to ultrasonic treatment. The thus-obtained ganglioside sample was loaded on the column. After 300 mL of Eluent I was passed through the column, GM1 was eluted with a linear concentration gradient generated with Eluents I and II (400 mL each). The eluate was collected as 10-mL fractions. Each of the fractions was subjected to TLC for the analysis of ganglioside components.

The TLC was developed with chloroform/methanol/0.2% KCl (5:4:1 (v/v)), and sprayed with orcinol sulfuric acid solution over the plate. Then, the plate was heated in an oven at 100° to 110° C. for 10 minutes to detect ganglioside. After coloring, the plate was subjected to a TLC chromatoscanner CS9300 (Shimadzu) to quantify ganglioside by determining absorbance at 540 nm.

Figure 4:
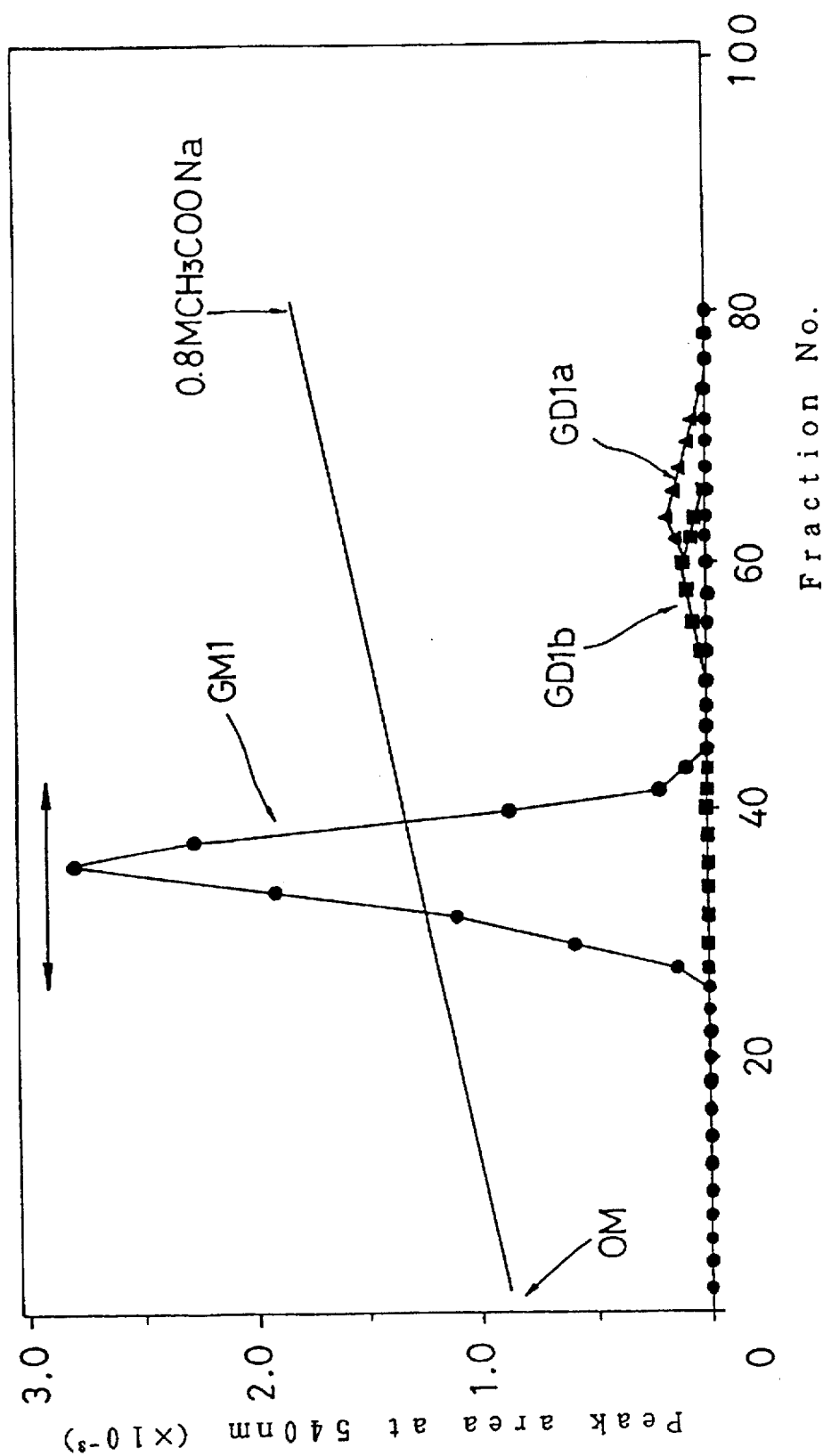
FIG. 4 shows the chromatogram on DEAE Sephadex A25 in Example 2.

As a result, GM1 was eluted in gradient elution fractions 26–43 (FIG. 4). The amount of GM1 thus purified was 175 mg by TLC.

The mass spectrometric analysis of the thus-obtained ganglioside using FAB-MS revealed that the ganglioside had a molecular weight of 1545, which confirmed the identity of the obtained ganglioside with GM1.

The above-presented data are summarized as follows: 500 mg of the crude ganglioside mixture contained about 215 mg of gangliosides, 40 mg of which was GM1. After the crude ganglioside mixture was cultured with Pseudomonas sp. YF-2 and the culture supernatant was passed through a reversed-phase chromatography column, the content of GM1 in the resulting eluate was as high as 200 mg. When the eluate was further purified by anion exchange chromatography, the amount of pure GM1 finally obtained was 175 mg, with a yield rate of 81% based upon the gangliosides in the starting crude ganglioside mixture.

Experimental Example
Effect of purified GM1 on the Development of Dendrites

Figure 5:
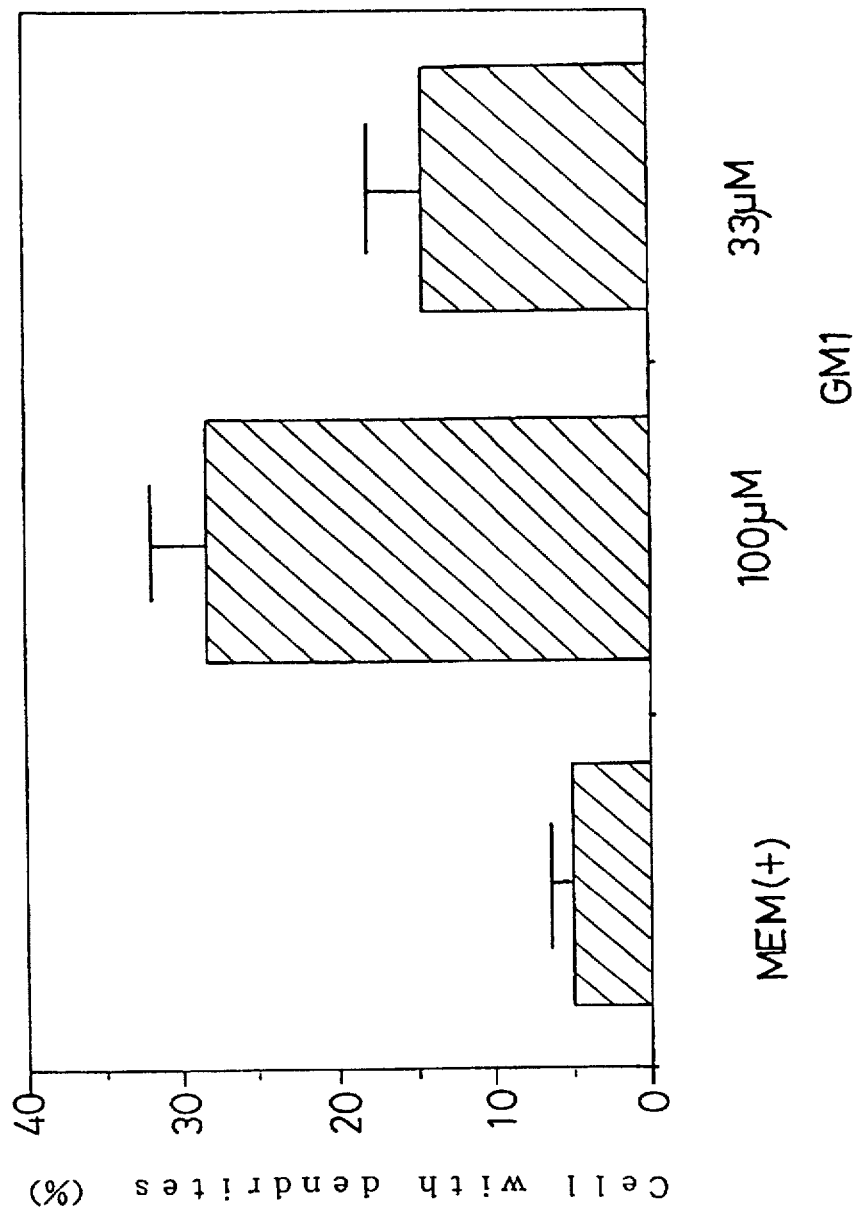
FIG. 5 shows the effect of purified GM1 on the development of dendrites.

The purified GM1 obtained in Example 2 was added to a medium containing serum (MEM medium containing 10% FCS (fetal calf serum) manufactured by Nissui) to make concentrations of 33 μM and 100 μM, where Neuro 2a cells (ATCC CCL-131), neuroblastoma cells, were cultured at 37° C. for 24 hours. After culture, the cells were photographed at random, and the number of cells with dendrites per 100 cells was counted to evaluate the degree of differentiation into neurons. As a result, it was found that the percentage of cells with dendrites was significantly increased by cultivating the cells in a medium containing the purified GM1 (FIG. 5). From the results of this Experimental Example, it was found that the effect of GM1 prepared in Example 2 on the development of dendrites can be obtained even in a serum-containing medium.

The present invention being thus described, it will be obvious that the same may be varied in many ways. Such variations are not to be regarded as a departure from the spirit and scope of the invention, and all such modifications as would be obvious to one skilled n the art are intended to be included within the scope of the following claims.

What is claimed is:

1. A method for producing monosialoganglioside GM1 comprising the step of contacting a crude ganglioside mixture with a microorganism which produces a sialidase, wherein said microorganism is a strain of Pseudomonas genus.

2. The method according to claim 1, wherein the microorganism is cultured in a medium containing the crude ganglioside mixture.

3. The method according to claim 2, wherein the cultivation is carried out at a temperature of from 20° to 35° C. and at a medium pH of 7.2 to 7.4.

4. The method according to claim 1, wherein the crude ganglioside mixture is added to a medium where the microorganism is grown.

5. The method according to claim 1, wherein the crude ganglioside mixture is prepared from a bovine brain.

6. The method according to claim 1, wherein the microorganism is isolated from oceanic samples selected from the group consisting of seaweed, sea water, and beach sand.

7. The method according to claim 1, wherein the sialidase has enzymological and physicochemical properties of (1) to (4):

(1) acting on a sialyl bond to release sialic acid;

(2) acting on GM3, GD1a and sialyl lactose (SA-Lac) to release sialic acid but not on GM1 and GM2 at all;

(3) having an optimal pH in the range of from 4.5 to 6.0 and being stable at temperatures of 37° C. or lower; and (4) being activated by manganese or barium and suppressed by mercury, copper, or iron.

8. The method according to claim 1, wherein said strain of Pseudomonas genus has the following bacterial features (1)–(19):

(1) rod-like shape, (2) motile, (3) Gram-negative, (4) grows in aerobic conditions, (5) does not grow in anaerobic conditions, (6) catalase positive, (7) oxidase negative, (8) negative O-F test, (9) no DNA decomposing ability,

(10) Negative gelatine liquefaction,

(11) Arginine dehydrogenase positive,

(12) does not grow at 5° C. and 37° C.,

(13) grows on glucose,

(14) does not grow on trehalose

(15) does not grow on L-Arginine,

(16) does not grow on L-Valine,

(17) does not grow on β-Alanine,

(18) does not produce fluorescent pigment, and

(19) 68.5% G-C content.

\* \* \* \* \*